(12) United States Patent
Payonk et al.

(10) Patent No.: US 7,558,416 B2
(45) Date of Patent: Jul. 7, 2009

(54) APPARATUS AND METHOD FOR MEASURING PHOTODAMAGE TO SKIN

(75) Inventors: Gregory Payonk, Flanders, NJ (US); Nikiforos Kollias, Skillman, NJ (US); Gabriela Oana Cula, Plainsboro, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 11/863,328

(22) Filed: Sep. 28, 2007

(65) Prior Publication Data

US 2008/0080755 A1  Apr. 3, 2008

Related U.S. Application Data

(60) Provisional application No. 60/848,767, filed on Oct. 2, 2006.

(51) Int. Cl.
  *G06K 11/00* (2006.01)
(52) U.S. Cl. .......................... 382/128; 600/476
(58) Field of Classification Search ................. 382/128; 600/476
  See application file for complete search history.

(56) References Cited

U.S. PATENT DOCUMENTS

| | | | |
|---|---|---|---|
| 4,170,987 A | 10/1979 | Anselmo et al. | |
| 4,592,726 A | 6/1986 | Brilliant | |
| 4,911,544 A | 3/1990 | Walsh | |
| 5,016,173 A | 5/1991 | Kenet et al. | |
| 5,241,468 A | 8/1993 | Kenet | |
| 5,331,551 A | * 7/1994 | Tsuruoka et al. | 382/128 |
| 5,363,854 A | * 11/1994 | Martens et al. | 600/477 |
| 5,456,260 A | 10/1995 | Kollias et al. | |
| 5,539,540 A | 7/1996 | Spaulding et al. | |
| 5,556,612 A | 9/1996 | Anderson et al. | |
| 5,640,957 A | 6/1997 | Kaminski | |
| 5,742,392 A | 4/1998 | Anderson et al. | |
| 5,785,960 A | 7/1998 | Rigg et al. | |
| 5,836,872 A | 11/1998 | Kenet et al. | |

(Continued)

FOREIGN PATENT DOCUMENTS

EP  0737932  10/1996

(Continued)

OTHER PUBLICATIONS

PCT Search Report PCT/US 02/35668, 2003.

(Continued)

*Primary Examiner*—Bhavesh M Mehta
*Assistant Examiner*—Stephen R Koziol (57) ABSTRACT

An apparatus and method for assessing photodamage has a digital imaging system for recording blue light imagining and in particular the green signal response intensity of the skin of a person, which is indicative of elastotic material and photodamage. Because the image data has a numerical intensity value, which may be expressed in RGB or L*a*b* colorspace, the image data taken from one image can be numerically compared to that of one or more other images and the image data is amenable to numerical and statistical analysis. Comparison to population profiles/image data permits an individual's image data to be characterized numerically, such as by a relative score or percentile rating. The image data can also be used to ascertain the degree of variation over a surface such as the face, with wider variation being indicative of greater photodamage.

16 Claims, 5 Drawing Sheets

U.S. PATENT DOCUMENTS

| | | | |
|---|---|---|---|
| 5,945,112 A | 8/1999 | Flynn et al. | |
| 6,018,586 A | 1/2000 | Kamei | |
| 6,021,344 A | 2/2000 | Lui et al. | |
| 6,032,071 A | 2/2000 | Binder | |
| 6,081,612 A | 6/2000 | Gutkowicz-Krusin et al. | |
| 6,148,092 A | 11/2000 | Qian | |
| 6,208,749 B1 | 3/2001 | Gutkowicz-Krusin et al. | |
| 6,215,893 B1 | 4/2001 | Leshem et al. | |
| 6,293,284 B1 | 9/2001 | Rigg | |
| 6,317,624 B1 | 11/2001 | Kollias et al. | |
| 6,436,127 B1 | 8/2002 | Anderson et al. | |
| 6,507,747 B1 | 1/2003 | Gowda et al. | |
| 6,510,366 B1 | 1/2003 | Murray et al. | |
| 6,597,392 B1 | 7/2003 | Jenkins et al. | |
| 6,603,552 B1 | 8/2003 | Cline et al. | |
| 6,728,560 B2 | 4/2004 | Kollias et al. | |
| 7,004,599 B2 | 2/2006 | Mullani | |
| 7,015,929 B2 | 3/2006 | Satomi et al. | |
| 2002/0059030 A1 | 5/2002 | Otworth et al. | |
| 2002/0065468 A1 | 5/2002 | Utzinger et al. | |
| 2002/0093698 A1 | 7/2002 | Kagawa | |
| 2003/0045916 A1 | 3/2003 | Anderson et al. | |
| 2003/0067545 A1 | 4/2003 | Giron et al. | |
| 2003/0086703 A1 | 5/2003 | Kollias et al. | |
| 2003/0086712 A1 | 5/2003 | Merola et al. | |
| 2003/0138249 A1 | 7/2003 | Merola et al. | |
| 2004/0006553 A1 | 1/2004 | de Vries et al. | |
| 2004/0077951 A1 | 4/2004 | Lin et al. | |
| 2004/0125996 A1 | 7/2004 | Eddowes et al. | |
| 2004/0146290 A1* | 7/2004 | Kollias et al. | 396/14 |
| 2004/0174525 A1 | 9/2004 | Mullani | |
| 2004/0186363 A1 | 9/2004 | Smit et al. | |
| 2004/0263880 A1 | 12/2004 | Ito et al. | |
| 2005/0131304 A1* | 6/2005 | Stamatas et al. | 600/476 |
| 2005/0146863 A1 | 7/2005 | Mullani | |
| 2005/0195316 A1 | 9/2005 | Kollias et al. | |
| 2005/0287040 A1 | 12/2005 | Giebeler et al. | |
| 2006/0092315 A1 | 5/2006 | Payonk et al. | |
| 2007/0002479 A1 | 1/2007 | Menke et al. | |
| 2007/0004972 A1 | 1/2007 | Cole et al. | |
| 2007/0005393 A1 | 1/2007 | Cole et al. | |

FOREIGN PATENT DOCUMENTS

| | | |
|---|---|---|
| EP | 0682236 | 11/1996 |
| EP | 1089208 | 4/2001 |
| EP | 1118845 | 7/2001 |
| EP | 1194898 | 3/2003 |
| EP | 1297782 | 4/2003 |
| EP | 1376444 | 1/2004 |
| EP | 1433418 | 6/2004 |
| EP | 1434156 | 6/2004 |
| EP | 1541084 | 6/2005 |
| GB | 2293648 | 4/1996 |
| JP | 7075629 | 3/1995 |
| WO | WO 96/16698 | 6/1996 |
| WO | WO 01/04839 | 1/1997 |
| WO | WO 97/05473 | 2/1997 |
| WO | WO 99/17668 | 4/1997 |
| WO | WO 97/47235 | 12/1997 |
| WO | WO 98/24360 | 6/1998 |
| WO | WO 98/37811 | 9/1998 |
| WO | WO 00/76398 | 12/2000 |
| WO | WO 01/22869 | 4/2001 |
| WO | WO 01/35827 | 5/2001 |
| WO | WO 01/45557 | 6/2001 |
| WO | WO 01/72216 | 10/2001 |
| WO | WO 02/061405 | 8/2002 |
| WO | WO 03/040878 | 5/2003 |

OTHER PUBLICATIONS

"Apparatus and Method for Viewing the Skin", U.S. Appl. No. 11/169,942, filed Jun. 29, 2005, Inventors: James Menke, et al.

"Calibration Apparatus and Method for Fluorescent Imaging", U.S. Appl. No. 11/863,345, filed Sep. 28, 2007, Inventors: Jeffrey Pote, et al.

"Apparatus and Method for Analyzing Skin Using L*a*b* Colorspace", U.S. Appl. No. 11/863,333, filed Sep. 28, 2007, Inventors: Gregory Payonk, et al.

"Method and Apparatus for Identifying Facial Regions", U.S. Appl. No. 11/863,323, filed Sep. 28, 2007, Inventors: Gregory Payonk, et al.

"Imaging Apparatus and Methods for Capturing and Analyzing Digital Images of the Skin", U.S. Appl. No. 11/863,342, filed Sep. 28, 2007, Inventors: Jeffrey Pote, et al.

Kollias, et al., "Fluorescence Photography in the Evaluation of Hyperpigmentation in Photodamaged Skin", Journal of the American Academy of Dermatology, vol. 36, No. 2, Part 1, 1997, pp. 226-230.

Muccini, et al., "Polarized Light Photography in the Evaluation of Photoaging", Journal of the American Academy of Dermatology, vol. 33, Nov. 1995, pp. 765-769.

Kollias, et al., "Optical Non-Invasive Approaches to Diagnosis of Skin Diseases", Optical Diagnostics in Dermatology, vol. 7, No. 1, Dec. 2002, pp. 64-75.

Kligman, et al., "Ultraviolet Photography Serves as Both Predictor and Educator", Cosmetic Dermatology, vol. 10, No. 9, Sep. 1997, pp. 31-33.

Anderson, "Polarized Light Examination and Photography of the Skin", Arch Dermatol, vol. 127, Jul. 1991, pp. 1000-1005.

Kollias, "Polarized Light Photography of Human Skin", Bioengineering of the Skin: Skin Surface Imaging and Analysis, Chapter 7, 1997, pp. 95-104.

Gartstein, et al., "Assessment of Visual Signs of Skin Aging", Bioengineering of the Skin: Skin Surface Imaging and Analysis, Chapter 3, 1997, pp. 331-345.

Hillebrand, et al., "Quantitative Evaluation of Skin Condition in an Epidemiological Survey of Females Living in Northern Versus Southern Japan", Journal of Dermatologic Science, vol. 27, Supp. 1, 2001, pp. S42-S52.

Stamatas, et al., "Non-Invasive Measurements of Skin Pigmentation in Situ", Pigment Cells Res. 17, 2004, pp. 618-626.

Kollias, et al., "Fluorescence Spectroscopy of Skin", Vibrational Spectroscopy 28, 2002, pp. 17-23.

Zonios, et al., "Skin Melanin, Hemoglobin, and Light Scattering Properties Can Be Quantitatively Assessed in Vivo Using Diffuse Reflectance Spectroscopy", The Journal of Investigative Dermatology, vol. 117, No. 6, Dec. 2001, pp. 1452-1457.

Stamatas, et al., "Blood Stasis Contributions to the Perception of Skin Pigmentation", Journal of Biomedical Optics, vol. 9, No. 2, Mar./Apr. 2004, pp. 315-322.

Gillies, "Fluorescence Excitation Spectroscopy Provides Information about Human Skin in Vivo", The Journal of Investigative Dermatology, vol. 115, No. 4, Oct. 2000, pp. 704-707.

Excerpt from website: www.courage-khazaka.de, Scientific Devices, 2005.

Excerpts from website: www.novatechcorp.com, 2004.

Excerpt from website: www.canfieldsci.com, 2006.

Z. Deyl, et al., "A Fluorescent Compound in Collagen and Its Relation to the Age of the Animal", Exp. Geront., vol. 5, 1970, pp. 57-62.

Na, et al., "Autofluorescence of Human Skin is Age-Related After Correction for Skin Pigmentation and Redness", The Journal of Investigative Dermatology, vol. 116, No. 4, Apr. 2001, pp. 536-540.

Leffel, et al., "In Vivo Fluorescence of Human Skin", Arch Dermatol, vol. 124, Oct. 1998, pp. 1514-1518.

Anderson, "Correspondence: In Vivo Fluorescence of Human Skin", Arch Dermatol, vol. 125, Jul. 1989, pp. 999-1000.

Odetti, et al., "Age-Related Increase of Collagen Fluorescence in Human Subcutaneous Tissue", Department of Internal Medicine and the Department of Physics, University of Genova, Italy, 1992, pp. 655-658.

Sandby-Moller, et al., "Skin Autofluorescence as a Biological UVR Dosimeter", Photodermatol Photoimmunol Photomed, 2004, pp. 33-40.

Kollias, et al., "Endogenous Skin Fluorescence Includes Bands That May Serve as Quantitative Markers of Aging and Photoaging", The Society for Investigative Dermatology, Inc., vol. 111, No. 5, Nov. 1998, pp. 776-780.

Brancaleon, "The In Vivo Fluorescence of Tryptophan Moieties in Human Skin Increases with UV Exposure and Is a Marker for Epidermal Proliferation", The Society for Investigative Dermatology, Inc., vol. 113, No. 6, Dec. 1999, pp. 977-982.

Tain, et al., "Aging and Effects of Ultraviolet a Exposure May Be Quantified by Fluorescence Excitation Spectroscopy In Vivo", The Society for Investigative Dermatology, Inc., vol. 116, No. 6, Jun. 2001, pp. 840-845.

Doukas, et al., "Fluorescence Excitation Spectroscopy for the Measurement of Epidermal Proliferation", Photochemistry and Photobiology, 74(1), 2001, pp. 96-102.

Barel, et al., "The Visi-Chroma VC-100®; A New Imaging Colorimeter for Dermatocosmetic Research", Skin Research and Technology, 7, 2001, pp. 24-31.

Excerpt from website: www.mcbi.nlm.hih.gov, "Long term exposure alters the collagen of the papillary dermis. Compoarison of sun protected and photoaged skin by northern analysis, immunohistochemical stainin, and confocal laser scanning microscopy", 1996.

Excerpt from website: www.ncbi.nlm.gov, "Noninvasive measurement of the effect of lifetime exposure to the sun on the aged skin,", 1994.

* cited by examiner

APPARATUS AND METHOD FOR MEASURING PHOTODAMAGE TO SKIN

CROSS-REFERENCE TO RELATED APPLICATIONS

This application claims the benefit of U.S. Provisional Patent Application Ser. No. 60/848,767 filed Oct. 2, 2006, the disclosure of which is incorporated herein by reference in its entirety.

FIELD OF THE INVENTION

The present invention relates to apparatus and methods for determining skin conditions and more particularly to such apparatus and methods which use digital imaging of persons to ascertain photodamage to the subject's skin.

BACKGROUND OF THE INVENTION

In assessing a person's skin from cosmetic and health perspectives, the amount of photodamage due, e.g., to sun exposure is an important factor. High exposure levels have been correlated to increased risk of skin cancer due to U-V radiation—induced cell mutations. Sun exposure also has detrimental cosmetic effects on the skin, e.g., the skin loses elasticity and color homogeneity, as evidenced by "age spots" or solar lentigenes. It is known that photodamage is associated with/indicated by internal changes to the skin which underlie the observed external skin attributes. One of these internal changes occurs in the superficial (papillary) dermis. More particularly, as persons age and their cumulative exposure to the sun increases, elastotic material accumulates in the superficial dermis, in the form of abnormally clumped elastic fibers accompanied by deformed collagen fibers.

Visualization and physical examination of a person's skin by a dermatologist and/or histological examination of a skin sample can yield information on the degree of photodamage, however, such techniques require expensive professional services are inconvenient, sometimes unpleasant and frequently do not result in a comprehensive, quantified measure of photodamage of a large area of the skin, such as the face, relative to a norm.

Various imaging systems have been proposed that photographically capture images of a person's face for analysis of the health and aesthetic appearance of the skin. Different images, e.g., captured at different times or under different lighting conditions, e.g., using different illumination and filtration frequencies, can be compared to one another to gain insight into the condition of the skin, e.g., at different times, such as before and after treatment, in order to ascertain trends in the condition of the skin. This was typically done by human operators inspecting the photographs to ascertain changes between them, based on color, texture, etc.

While photographic skin imaging and analysis by human inspection is quite useful, it remains an objective in the art to conduct such analyses more insightfully without dependence upon professional evaluation and Judgment and in a more objective and reproducible manner.

SUMMARY OF THE INVENTION

The limitations of prior art methods and apparatus for ascertaining and assessing photodamage in persons are overcome by the present invention which includes an apparatus for detecting elastotic material in the skin by measuring the green response thereof to illumination with blue light. In an embodiment of the present invention, the intensity of the green signal response is recorded in a digital image as pixel intensity values. Given the accumulation of such data for numerous people, population norms and profiles can be assembled through quantitative analysis, to which individuals can be quantitatively compared. In accordance with an embodiment of the present invention, one useful method of quantitative analysis is to ascertain the distribution of green intensity response across the facial region, greater variations in intensity being indicative of greater photodamage.

DETAILED DESCRIPTION OF THE INVENTION

Figure 1:
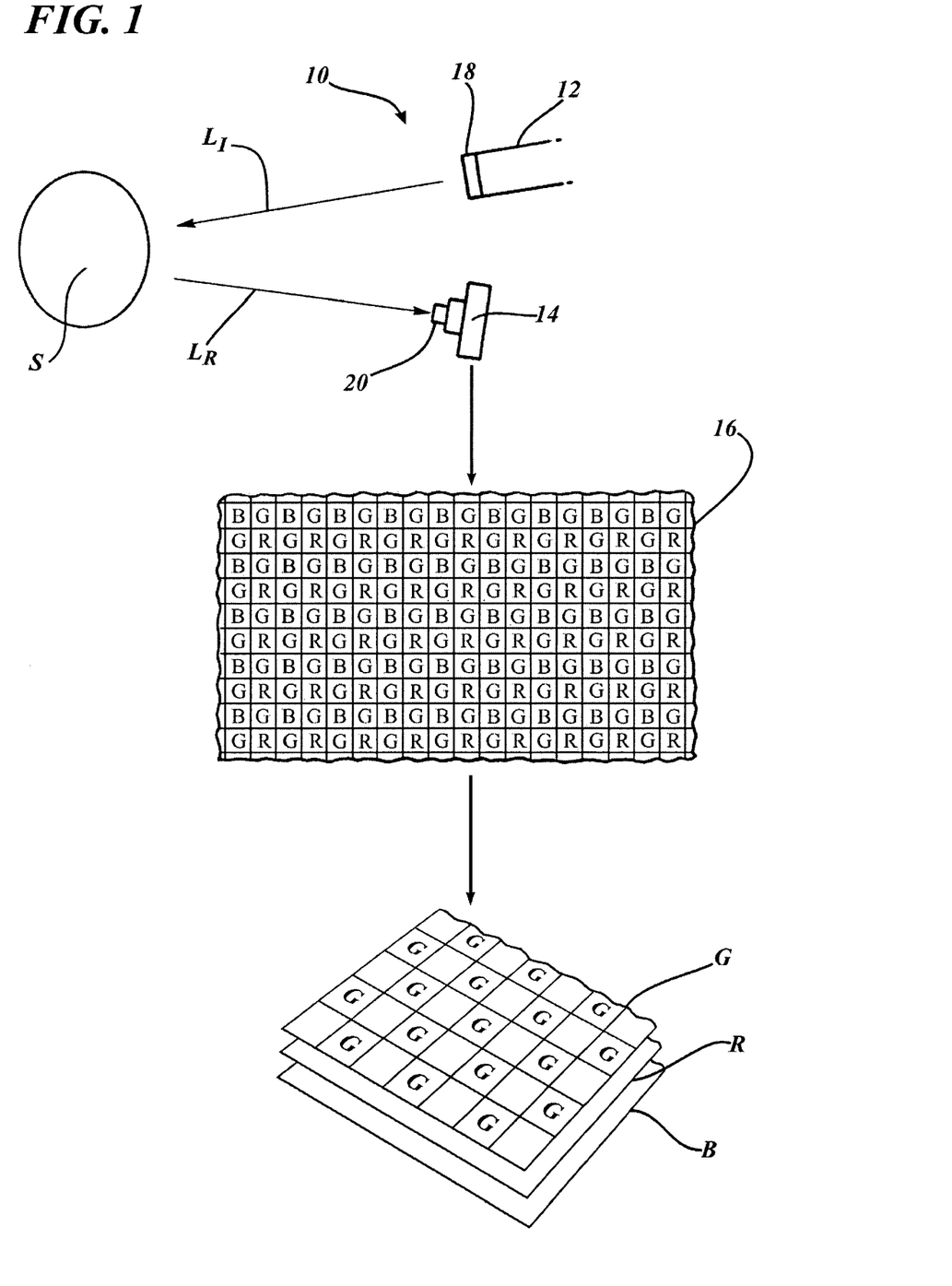
FIG. 1 is a diagrammatic view of a digital imaging system in accordance with the present invention.

FIG. 1 diagrammatically illustrates a digital imaging apparatus 10 having a source of illuminating light 12 (e.g., a photo flash) and a digital camera 14. An image of the subject S is recorded by the camera 14 in the form of a matrix 16 of pixel values in RGB format (red, green, blue). The matrix 16 of values is typically produced by a Bayer-filtered close-coupled display CCD and the information is stored in a memory device, such as random access memory (RAM) or on a flash memory card. The RGB data can be separated into channels or planes, R, G and B, one plane for each color. Various frequencies of illuminating light $L_I$ disposed at varying positions relative to the subject S may be used to capture digital images of the subject S in order to capture different information about the skin of the subject. Filters 18, 20 may be employed on the light 12 and the camera 14, respectively, to control the light frequency/polarity of light $L_I$ which is projected on the subject S, as well as controlling the light $L_R$ (reflected or emitted from the subject S), which is admitted into the camera 14. Imaging of this type is described at length in co-pending U.S. patent application Ser. No. 10/008,753, entitled, "Method of Taking Images of the Skin Using Blue Light and the Use Thereof", which was published as United States Application Publication No. US 2004/0146290 A1, U.S. patent application Ser. No. 10/978,284 entitled "Apparatus for and Method of Taking and Viewing Images of the Skin," which was published as United States Patent Application Publication No. US 2005/0195316 A1 ("U.S. Publication No. 2005/0195316"), application Ser. No. 11/169,813 entitled "Skin Imaging System with Probe", which was published as United States Application Publication No. US 2006/0092315 A1 ("U.S. Publication No. 2006/0092315"), all of which are incorporated by reference herein in their entirety. The foregoing applications disclose various correlations between skin condition and the images produced by various photographic parameters, i.e., specific combinations of illuminating light, filters 18, 20, etc. The skin response to different illuminating frequencies, angles, polarity etc. can reveal information about skin condition and this evidence of skin condition can be recorded and recalled in digital images for purposes of analysis.

Since the images recorded are in digital form, i.e., in numerical pixel intensity values, the images lend themselves to quantitative analysis. For example, instead of just noting that the cheek of a subject whose image is taken at time T1 is more or less green in color in an image of the person taken at time T2, as discerned by a skilled human observer, the values of the intensity of the green pixels in the specific area of the cheek at times T1 and T2 may be quantitatively compared. For example, the two values may be numerically analyzed to quantify the actual change in intensity for that pixel or pixels in that region. Digital image quantification can be used to discern average values for the skin in specified regions, e.g., by summing the values of pixels in the specific region and then dividing by the number of pixels. In this manner, a whole area of the face may be characterized quantitatively. Various other quantified analyses may be conducted, e.g., the imaged area of skin may be tested for standard deviation in pixel intensity or the RGB data may be converted to L*a*b* coordinate space and the a* values indicative of green coloration mathematically analyzed (e.g., the a* values of subsequent images can be directly compared—subtracted) to ascertain a change in greenness. The conversion of RGB image data to L*a*b* data is described at length in a co-pending application filed on Oct. 2, 2006 as U.S. Provisional Application No. 60/848,768 contemporaneously herewith entitled, "Apparatus and Method for Analyzing Skin Using L*a*b* Colorspace", which is incorporated in its entirety herein by reference.

Given the capability of quantifying digital imaging results/data and the capacity for obtaining large samples of image data over time and across population groups, this data may be quantitatively analyzed to ascertain relationships and tendencies within these population groups, e.g., to establish normative skin conditions. The present invention is directed to ascertaining and apprising the level of photodamage in an individual or a population of individuals. Of course the same methods of data collection through digital imaging and numerical analysis of the data collected both from populations and from individuals may be utilized to draw conclusions pertaining to other parameters of skin condition.

As applied to the analysis of photodamage, the medical literature indicates a correlation between the number of hours of sun exposure to the level of photodamage. Related correlations exist pertaining to age and photodamage, (viz., the greater the person's age, the more photodamage is likely), the time that persons spend in particular latitudes (those with greater sun exposure having more photodamage), skin type by amount of melanin (greater pigmentation leading to less photodamage), etc. The present invention therefore recognizes that various photodamage—sensitive population groupings may be made for the purpose of assessing the likelihood of photodamage and that the level of photodamage may be assessed and quantified for samples of these populations to identify and quantify the predictive factors that a person may encounter or possess that effects photodamage. Accordingly, the present invention recognizes the utility of conducting large scale imaging studies involving diverse people and recording their various attributes and experiences to establish a database of digital image samples that may be subject to quantified analysis. This quantified analysis may then be used to quantify the various risk factors leading to photodamage, both in isolation and in combination.

Figure 2:
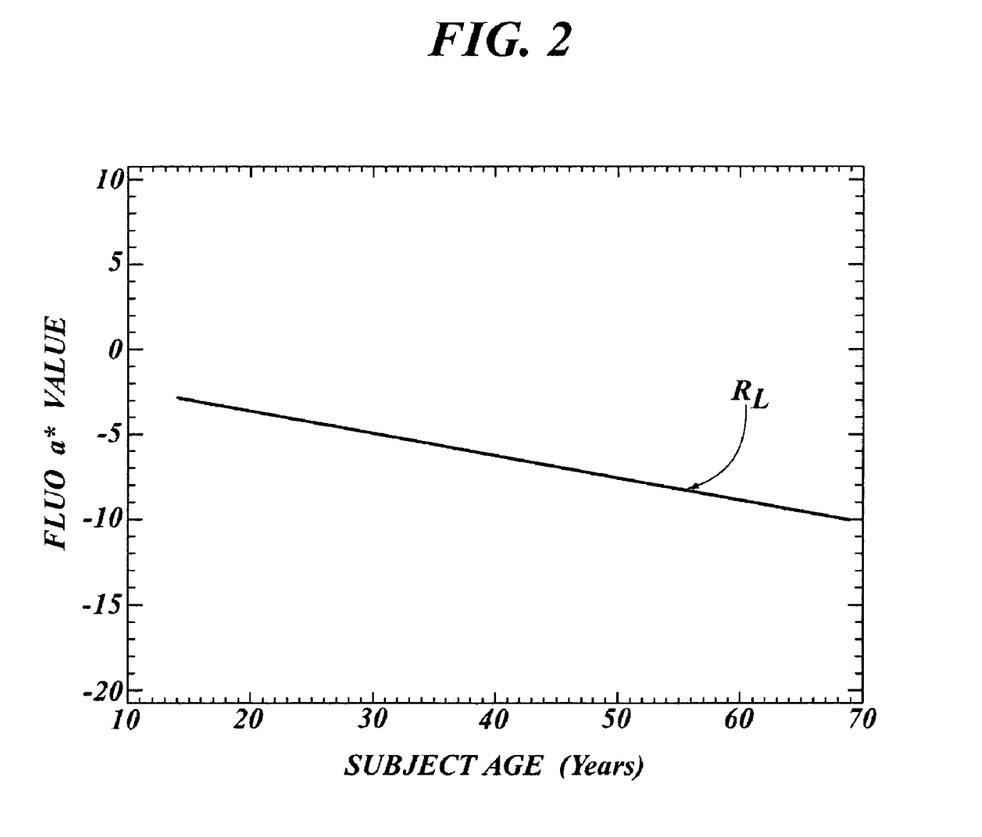
FIG. 2 is a graph of a* value vs. age for a first population of subjects whose digital images were captured.

As to predictive indicators of photodamage accessible through digital imaging, the present invention recognizes that the intensity of the green fluorescence response of the skin to illumination with blue light is an indicator for the presence of elastotic material. As noted above, photodamage is correlated with the presence of elastotic material. FIG. 2 is a graph of a* value by age for 7,825 subjects. The slope of the regression line $R_L$ is negative, indicating that, as subjects age, the a* value decreases, corresponding to an increase in "greenness" indicative of greater photodamage.

Given the foregoing correlation between green fluorescence signal intensity in response to blue light, and the capability to quantify same from the analysis of digital images, an individual seeking information concerning his/her level of photodamage can present themselves for one or more sessions of digital imaging under blue light, i.e., light having a wavelength from about 380 nm to about 430 nm. For example, the imaging may be conducted with one or more flashes 12 having interference filters 18. The camera 14 may also have a filter 20, e.g., a long pass filter to eliminate wavelengths below 400 nm, such as a GG-420 or GG-440 filter from Schott Glass Technologies and Wratten No. 8 from Eastman Kodak. After capturing the digital image in RGB format, the green signal data G is isolated and analyzed.

For all pixels of any image, there is an associated pixel intensity, which is determined by the photo-response of a photosensitive element, e.g., a voltage induced in a capacitor element in a CCD array. This image profile and the underlying intensity data may be used to quantitatively assess the level of photodamage present in the subject S whose image was captured in the image.

As with many other measurements, a measure of the extent or degree of photodamage has enhanced meaning when compared to some standard, such as the norm or mean for a relevant population. In comparison to this norm, an individual's state can be characterized as better or worse, ranked by percentile, or placed within a scale, e.g., a 1-to-10 ranking. This numerical characterization can then be associated with outcome likelihoods established by statistical studies of relevant populations. For example, if an individual is found to have photodamage that is 50% less than the norm of persons with similar age, pigmentation and geographic location, and statistical studies indicate that such person have a low chance of suffering from photodamage-related disease or conditions, such as melanoma, wrinkling or age spots when they are 60 years of age, then their low score would be an indicator that their risk for such conditions is low (—if they continue in their present course of behavior). Conversely, a person who proves to have a relatively high numerical photodamage score may be a greater risk and therefore behavior modification and/or treatment of the condition may be advisable.

In order to establish a standard of comparison, the individual may identify certain data about themselves, in particular regarding any data that has been shown by population studies to be predictive of photodamage, such as age, pigmentation (race) years of residency in specific geographic locations/latitudes, lifestyle and habituation as to outdoor activities, use of sunscreen, etc. Given this data, the relevant data can be extracted from the database of collected analyzed digital images and other sources of information concerning photodamage outcomes and levels associated with such factors. The individual's green intensity response data can then be compared to the accumulated population data to develop a score or percentile of photodamage relative to the overall population and/or relative to any particularly relevant population(s). In this manner, photodamage can be quantified by a number and the number can be representative of variations from the norm established by different populations of interest.

Besides, comparison to population groups, the subject person may present themselves for more than one imaging session spaced in time to discern or monitor changes in the level of their photodamage and the efficacy of skin treatments directed to reversing photodamage, e.g., the use of Trentinoin/Retin A.

In analyzing the skin of a person's face, it is beneficial to examine specific regions of the face for specific associated attributes, since the different regions of the face are specialized in form and function and interact with the environment differently. For example, the skin covering the upper surface of the nose is exposed to the most direct and intense rays of the sun, i.e., those emitted from late morning to early afternoon and therefore has a greater likelihood of photodamage. In contrast, the skin of the eyelids is shielded from the sun due to the bunching of the eyelid and retraction into the eye socket when the eye is open. Photodamage will therefore vary more strongly from skin region to region in a person who has been exposed to more radiation, i.e., the sun exposed areas will exhibit much higher photodamage than non-exposed areas, whereas in a person with limited sun exposure, the areas of the face with greater natural sun exposure will differ less from the areas of less natural sun exposure. Wide variations of green intensity signal across the face (or other body areas, e.g., dorsal vs. volar surfaces) is therefore an indicator of photodamage, because it indicates greater sun exposure.

In a similar manner, the response of skin to sun exposure can vary over a skin surface, such as the face or the back. Persons with little pigment in their skin and low capacity for melanin production tend to freckle, which indicates an uneven response of the skin to sun exposure and uneven photodamage over the surface. As a result, high variability of the green response signal to blue light is an indicator of photodamage (associated, e.g., with the freckled skin of a person with low pigment levels.

Figure 3:
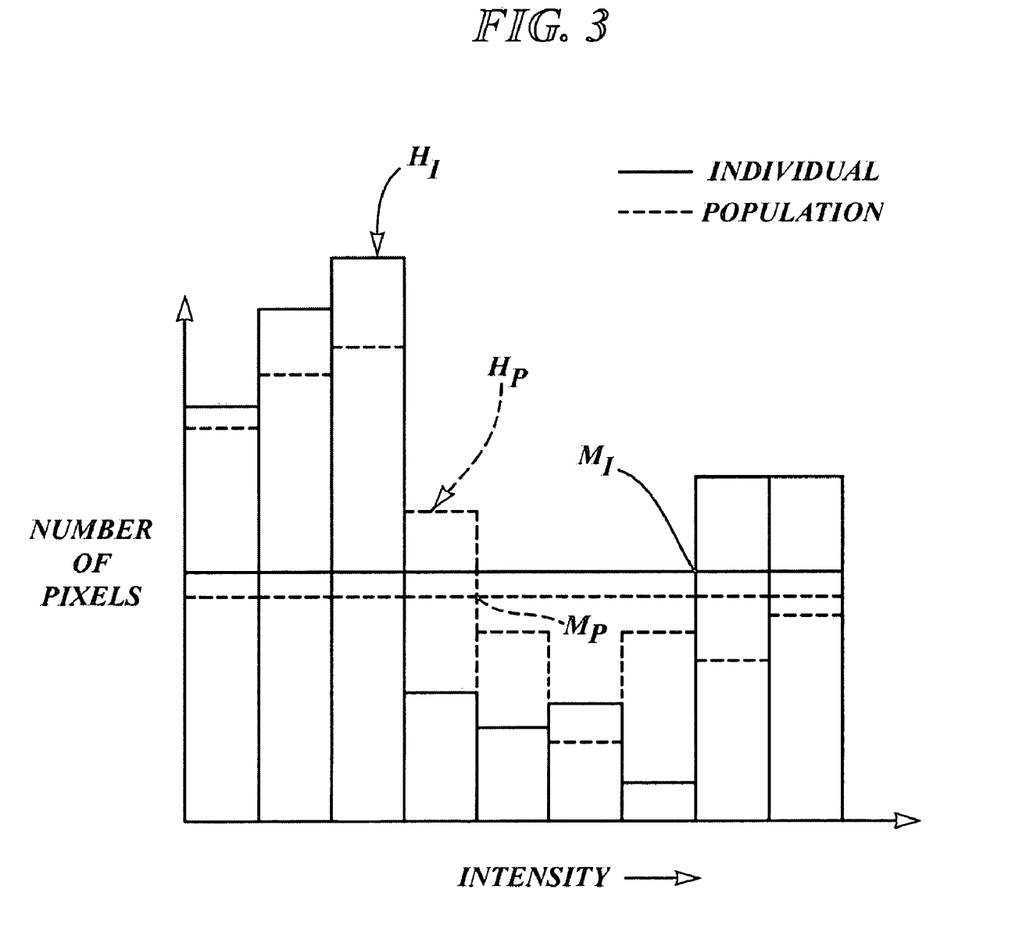
FIG. 3 is a histogram of pixel intensity for a specific skin region for an individual and for a population.

FIG. 3 shows an exemplary fictional histogram of pixel counts for different levels of green fluorescence response pixel intensity distributed over an area of the skin, such as the facial region. The solid lines indicate readings for an individual $H_I$ and the dotted lines indicate those values associated with a population $H_P$. As can be appreciated from the graph, the median pixel intensity $M_P$ for the population is lower than the median intensity $M_I$ for the individual. This is one indication of greater photodamage. Furthermore, the individual's pixel intensity groups $H_I$ vary farther from the median for the individual $M_I$ than the intensity groups $H_P$ of the population vary from the population median $M_P$. This is an indication that the standard deviation of pixel intensity of the individual is greater than the standard deviation of pixel intensity for the larger group (population). As noted above, this is also an indicator that the individual has a higher than normal amount of photodamage, in that he/she exhibits a wider variation in green signal intensity over the facial region. This would be analogous to freckling.

Figure 4:
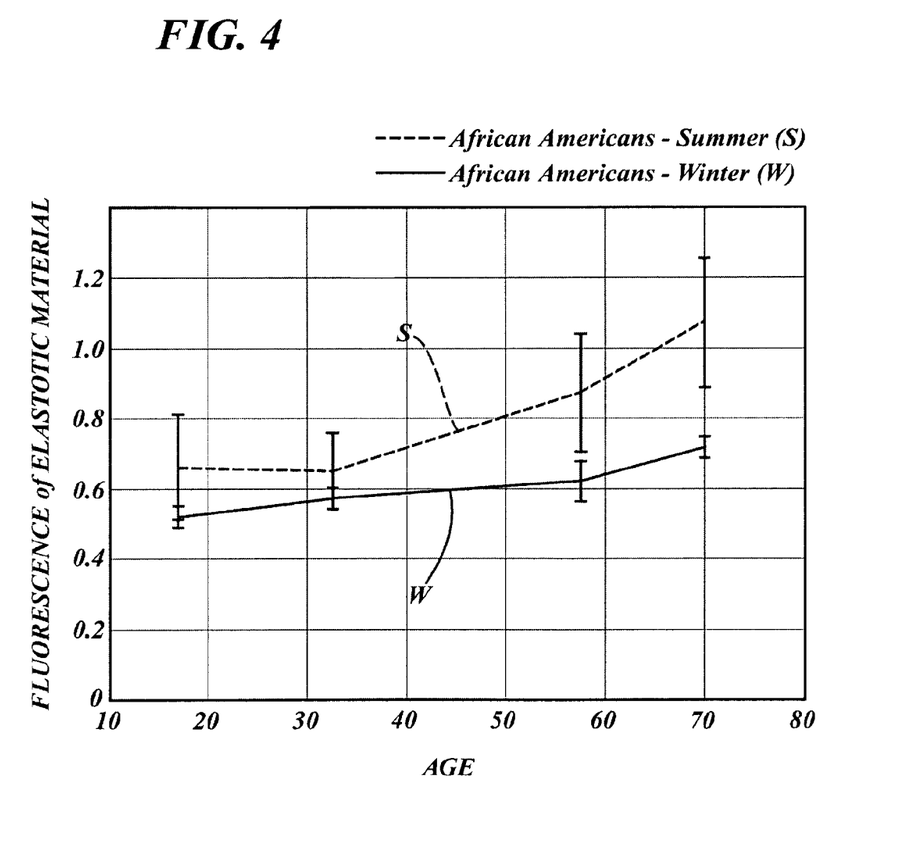
FIG. 4 is a graph of fluorescence of elastotic material vs. age for a second population sample.
Figure 5:
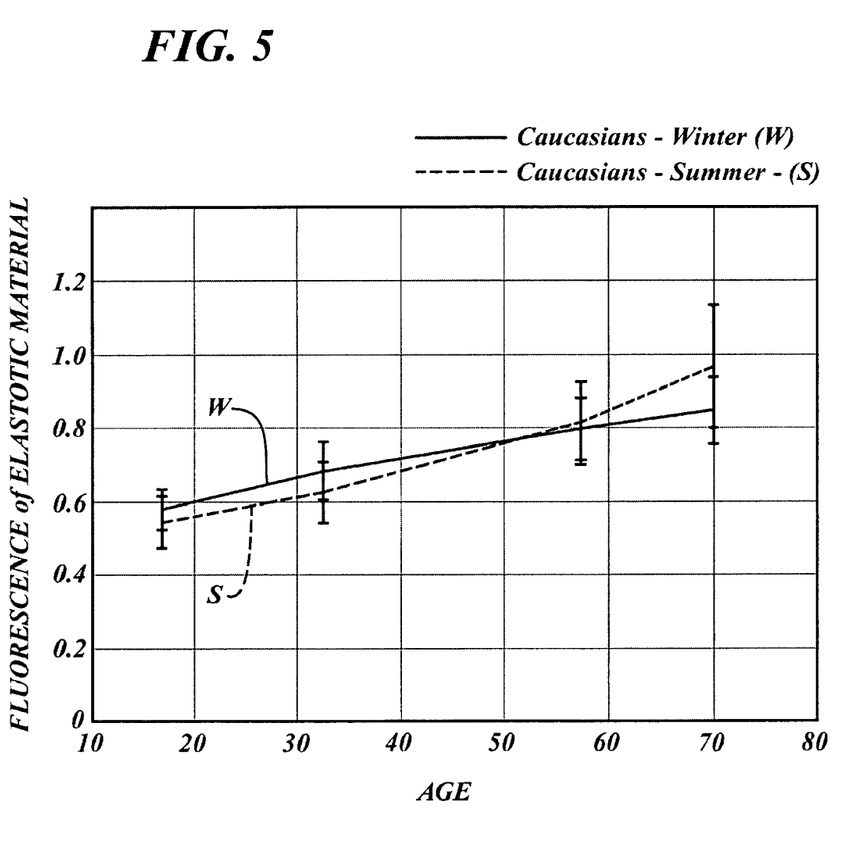
FIG. 5 is a graph of fluorescence of elastotic material vs. age for a third population sample.

FIGS. 4 and 5 show fluorescence of elastotic material vs. age for two groups of persons, African Americans and Caucasians, respectively. In each of FIGS. 4 and 5, the sample size was 200 persons and testing was conducted in the summer (S) and in the winter (W). There is a seasonally varying level of photodamage present in both groups due to the increase in sun intensity and exposure in the summer and a corresponding decease in the winter. The following is a detailed description of the processing involved in computing the graphs.

For each subject, a region of interest on the face has to be defined to ensure that the images do not present signals from other fluorophores besides the elastotic material, such as horn and porphyrin. Also, one has to make sure that the assessment of fluorescence is based on analogous regions on the face, to guarantee that the quantification is consistent across various subjects. From visual inspection of the images, the subjects were evaluated to insure that each consistently presented measurements uncompromised by the presence of "horn" and "porphyrin". The measurements were taken from the cheek, under the eye. For all subjects, the region of interest (ROI) was defined as a rectangular area on the left cheek, under the eye, with the top left corner of the ROI aligned horizontally with the center of the eye and aligned vertically with the center of the nose.

In order to quantify the elastotic material for each ROI, the green channel (RGB data) of the blue fluorescence (BF) image was selected since the elastin crosslinks fluoresce at the green region of the spectrum. Furthermore, the fluorescence signal as defined by the green channel of the BF images has to be corrected such that the measurement is not affected by the facial pigmentation. The green channel of the visible image, corresponding to the same ROI on the face, was used to normalize the signal. The corrected-for-pigment green channel of the BF image was averaged over the area of the ROI. The extracted number is referred to as the "background blue fluorescence index", denominated by BBFI.

The BBFI for each of the subjects in the database was extracted and the average and the standard deviation of the BBFI were computed to analyze the dependency of the BBFI as a function of the age and the skin type. The results are summarized in the two graphs of FIGS. 4 and 5. FIG. 4 shows BBFI as a function of age, for African-American skin, for summer and winter and FIG. 5 shows BBFI as a function of age, for Caucasian skin, for summer and winter.

It should be understood that the embodiments described herein are merely exemplary, and that a person skilled in the art may make many variations and modifications without departing from the spirit and scope of the invention. All such variations and modifications are intended to be included within the scope of the invention.

We claim:

1. A method for detecting photodamage to skin, comprising the steps of:
   (A) providing an imaging apparatus having a digital camera, a source of light of 380 nm to 430 nm;
   (B) exposing skin to light in the approximate wavelength range of 380 nm to 430 nm;
   (C) capturing the green response of the skin to the light of step (B) in a digital image with the camera;
   (D) isolating the green response attributable to elastotic material beneath the outer surface of the skin recorded in the digital image by the steps of identifying a region of interest in the digital image corresponding to an area of skin having low horn and low porphyrin and isolating the green response of elastotic material from the green response of skin pigment and;
   (E) measuring the green response attributable to elastotic material beneath the outer surface of the skin recorded in the digital image.

2. The method of claim 1, wherein said step of identifying includes identifying a plurality of regions of interest on the skin imaged; taking at least one image of a plurality of the regions of interest; and comparing the resultant green response recorded in the at least one image for the plurality of regions.

3. The method of claim 2, wherein variations of green response from region to region are quantitatively interpreted as indicative of photodamage.

4. The method of claim 3, wherein the variation of green response from region to region is quantified by calculating the standard deviation thereof.

5. The method of claim 1, further including repeating steps (A) through (E) a plurality of times for skin of different persons who form a statistically significant group to establish a group model.

6. The method of claim 5, further comprising the steps of identifying a group model which is predictive for an individual and comparing the green response of the individual to the predictive group model.

7. The method of claim 6, wherein the relationship between the green response of the individual and the green response of the group model is expressed as a percentile rank.

8. The method of claim 5, wherein the persons are selected for inclusion in a group based upon at least one of the following: race, skin pigmentation, geographic location of residence and extent of sun exposure.

9. The method of claim 5, further including the step of performing said steps (A) through (E) in a plurality of different seasons which have significantly different levels of solar radiation.

10. The method of claim 5, further including the steps of identifying a plurality of regions of interest on the skin, then for each person in the group, taking at least one image for each of the regions of interest and comparing the resultant green response stored in the images for the plurality of regions.

11. The method of claim 1, further including the step of converting an imaging colorspace in which the green response is first recorded to L*a*b* colorspace, and using the a* axis in measuring the green response.

12. The method of claim 1, further including the step of performing steps (A) through (E) a plurality of times yielding corresponding green responses, from which a trend in the person's photodamage may be discerned.

13. The method of claim 12, wherein the trend may be used to assess the person's response to treatment of the photodamage.

14. The method of claim 1, wherein the step of isolating the green response of elastotic material includes capturing images in white light and in blue light then normalizing image data from an image taken in white light and image data from an image taken in blue light, wherein the respective white and blue light images are of an area of skin having substantially the same pigment and elastotic material characteristics.

15. The method of claim 1, wherein the region of interest corresponds to an area of skin on the cheek under the eye.

16. A method for detecting photodamage to skin, comprising the steps of:
(A) selecting a plurality of persons on the basis of skin similarity;
(B) identifying a plurality of facial regions having different sun-exposure probability;
(C) for each of said plurality of persons, exposing each of the plurality of skin regions to light in the approximate wavelength range of 380 nm to 430 nm and capturing a plurality of digital images with a digital camera, each digital image having green response data corresponding to the green response of the skin imaged;
(D) converting the green response data to a* equivalents in L*a*b* colorspace, said green response data being at least partially attributable to the elastotic material beneath the surface of the skin, the presence of elastotic material being indicative of photodamage;
(E) quantitatively analyzing the green response data primarily attributable to elastotic material differentiated from that attributable to skin pigment and porphyrins to ascertain at least one of the mean of the green response data for all images and the standard deviation between regions for the plurality of persons;
(F) comparing at least one of the mean and the standard deviation of the green response data of an individual to the quantitatively analyzed green response data of Step (E) to show how the individual's photodamage compares to that of the plurality of other persons, thereby giving a relative measure of photodamage.

* * * * *